United States Patent
Duncan et al.

(10) Patent No.: US 7,226,338 B2
(45) Date of Patent: Jun. 5, 2007

(54) MILLING MACHINE

(75) Inventors: Rod Duncan, Grass Valley, CA (US); Joel Witt, Dallas, TX (US); Mark Quadling, Plano, TX (US); Henley Quadling, Dallas, TX (US); Jeffrey Prince, Grass Valley, CA (US); Branko Bem, Plano, TX (US); Rui Xu, Plano, TX (US); Kirk Ray, Plano, TX (US); Basil Haymann, Dallas, TX (US); Anthony Starfield, St Paul, MN (US)

(73) Assignee: D4D Technologies, LLC, Richardson, TX (US)

( * ) Notice: Subject to any disclaimer, the term of this patent is extended or adjusted under 35 U.S.C. 154(b) by 181 days.

(21) Appl. No.: 10/917,069

(22) Filed: Aug. 12, 2004

(65) Prior Publication Data

US 2006/0035775 A1   Feb. 16, 2006

(51) Int. Cl.
*B24B 49/00* (2006.01)
*B24B 51/00* (2006.01)

(52) U.S. Cl. .............. 451/6; 451/8; 451/65; 451/132; 451/190; 451/262; 451/451

(58) Field of Classification Search ............... 433/55, 433/218, 223; 451/5, 6, 8–11, 41, 57, 58, 451/65, 66, 132, 190, 194, 262, 264, 265, 451/451, 457

See application file for complete search history.

(56) References Cited

U.S. PATENT DOCUMENTS

| | | | | |
|---|---|---|---|---|
| 4,411,626 | A | * | 10/1983 | Becker et al. ............ 433/223 |
| 4,514,934 | A | * | 5/1985 | Ray et al. ................... 451/7 |
| 4,575,805 | A | * | 3/1986 | Moermann et al. ........ 700/163 |
| 6,004,195 | A | * | 12/1999 | Jaslow et al. .............. 451/391 |
| 6,102,023 | A | * | 8/2000 | Ishiwata et al. ........ 125/13.01 |
| 6,135,854 | A | * | 10/2000 | Masumura et al. ........... 451/6 |
| 6,454,636 | B1 | * | 9/2002 | Iwabuchi .................... 451/53 |
| 6,953,383 | B2 | * | 10/2005 | Rothenberger .............. 451/11 |

* cited by examiner

*Primary Examiner*—Timothy V. Eley
(74) *Attorney, Agent, or Firm*—David H. Judson

(57) ABSTRACT

The improved milling machine makes use of individually controlled x-axis, y-axis, and z-axis carriages. These carriages provide positive and precise control of the position of the cutting tools and the blank to be cut. A tool changer allows the tools to be changed to accommodate other materials. A camera is used to detect wear on the tools.

12 Claims, 8 Drawing Sheets

MILLING MACHINE

TECHNICAL FIELD OF THE INVENTION

The present invention relates to an improved milling machine that is used to mill a crown or dental implant from a blank. The milling machine is adapted to receive instructions from a separate scanner that provides a memory in the milling machine with data on the outer and inner contours for the milled crown.

BACKGROUND TO THE INVENTION

One of the most common procedures for a dentist is the repair of a broken tooth. When a tooth is broken, a portion of the enamel comes off, exposing the dentin underneath. The dentin must be covered to prevent the dentin from becoming infected. The dentist will grind a portion of the remaining enamel away to prepare the tooth for a crown. Once the grinding procedure is complete, a reduced stump remains and a mold of the stump is made with a quick setting mold material. Further a mold of the adjacent teeth and the opposing teeth are also made. Then a temporary crown in placed on the stump. The temporary crown has been partially customized to fit over the stump and to mesh with the opposing teeth. However, due to traditional time constraints, the temporary crown rarely feels as natural as the original tooth. Further, the temporary crown must be affixed to the stump with a temporary fixative.

With the mold as a guide, an outside laboratory will prepare a permanent crown. The permanent crown may be made of porcelain, gold, ceramic, or other metal or substance. This process usually takes at least three weeks to complete. During this time, the patient must function with the temporary crown. Unfortunately, there is a risk that the temporary crown may loosen and be swallowed or otherwise lost by the patient. Even if it only loosens, bacteria can gain access to the dentin for a time and cause more serious dental health issues. Also, once the permanent crown is available for placement, the temporary crown must be removed. This requires the dentist to twist the temporary crown off the stump, exerting a significant torque to the roots. Even then, if the permanent crown is misshaped, then it may need to be removed again and remade.

A need exists for a method of improving the speed of producing a permanent crown for a patient. Indeed, if the crown could be produced while the patient waited, it would be a great savings for the patient and the dentist both. Moreover, it would also be beneficial to eliminate the need to make a temporary crown at all.

Sirona Dental Services GmbH, of Bensheim Germany produces a milling machine specifically for producing porcelain crowns. It is disclosed in U.S. Pat. No. 6,394,880 discloses one aspect of this milling machine. It allows for the use of two milling bits to simultaneously work a blank to form it into a permanent crown. The mill bits are located on opposite sides of the blank and can move in an x-, y-, and z-plane. However, the bits can not be changed on demand to accommodate a different blank material. Also, there is no method disclosed for determining the bit wear to warn the dentist that the crown's dimensions may be skewed due to bit wear.

The Sirona patent illustrates a portion of a larger milling machine known as the CEREC. The CEREC has several other drawbacks. First, it has only a wireless connection with an intraoral digitizer used to make the measurements of the stump and adjacent teeth. Once the measurements are made, the intraoral digitizer cannot be used until the crown is finished. Therefore, a need exists for a milling machine that includes a memory that can store the required data thereby freeing the intraoral digitizer to be used again. Further, the CEREC device is flawed in its failure to minimize vibration that affects the quality of the milling. Even minor vibration can create many microns of error on the surface of the crown.

SUMMARY OF THE INVENTION

The present invention overcomes many of the defects of the prior art and allows the dentist to mill a superior permanent crown or other dental inlay while the patient waits. This reduces the amount of time for the patient in the dentist chair, thereby allowing the dentist to schedule more patients. Further, it is a significant time savings for the patient. The milling machine can be located at the dentist office. However, it could also be located at a traditional dental lab. In this event, the lab would receive the data outlining the contours for the crown or the inlay. It would still be able to supply a superior crown or inlay in less time than traditionally experienced.

The present milling machine is characterized by a robust and sturdy frame that minimizes any vibration. This helps ensure the highest quality end product. Further, the spindles that rotate the milling bits are located on a common rail, giving the device the ability to move the tools in the x-axis. The blank is releasably attached to a mandrel. The mandrel is secured to a subassembly that allows motion in the y-axis and the z-axis. The milling machine includes a CPU and memory for storing the data on the contour of the crown or inlay. Further, the milling machine has a water reservoir for settling any particulate that becomes entrained in the water used to cool and rinse the blank during milling.

Tools used to mill the blank can be changed using a novel automatic tool changer. The ability to engage different tools also allows for the use of different blank materials, from hardened metals to ceramics to porcelain to gold. Further, a camera or other sensing device can be used to monitor wear experienced by the tools. The blank is held by a mandrel that engages a frame within a work area that is easily accessible to a technician or the dentist. While this disclosure focuses on the production of crowns, it should be understood that this term is being used broadly. Indeed, while a crown is one of the preferred items for milling, this improved milling device could be used to produce inlays, onlays, coping, framework, bridges, implants, implant abutments, veneers, and overlays.

BRIEF DESCRIPTION OF THE DRAWINGS

The novel features believed characteristic of the invention are set forth in the appended claims. The invention itself, however, as well as a preferred mode of use, further objectives and advantages thereof, will best be understood by reference to the following detailed description of an illustrative embodiment when read in conjunction with the accompanying drawings, wherein:

DETAILED DESCRIPTION OF THE DRAWINGS

This inventive milling machine is sized to fit on the countertop of a dentist office or in a lab. Its generally compact size however does not mean that the quality of end product is diminished. Instead, the milling machine is built so robustly that it will produce the highest quality crowns and inlays. An intra-oral digitizer is used to measure the dimensions of the prepared tooth, as well as the adjacent and opposed teeth. Software within the digitizer constructs an outer contour that meshes with the adjacent and opposing teeth. The design is approved by the dentist and then conveyed to the milling machine.

Figure 1:
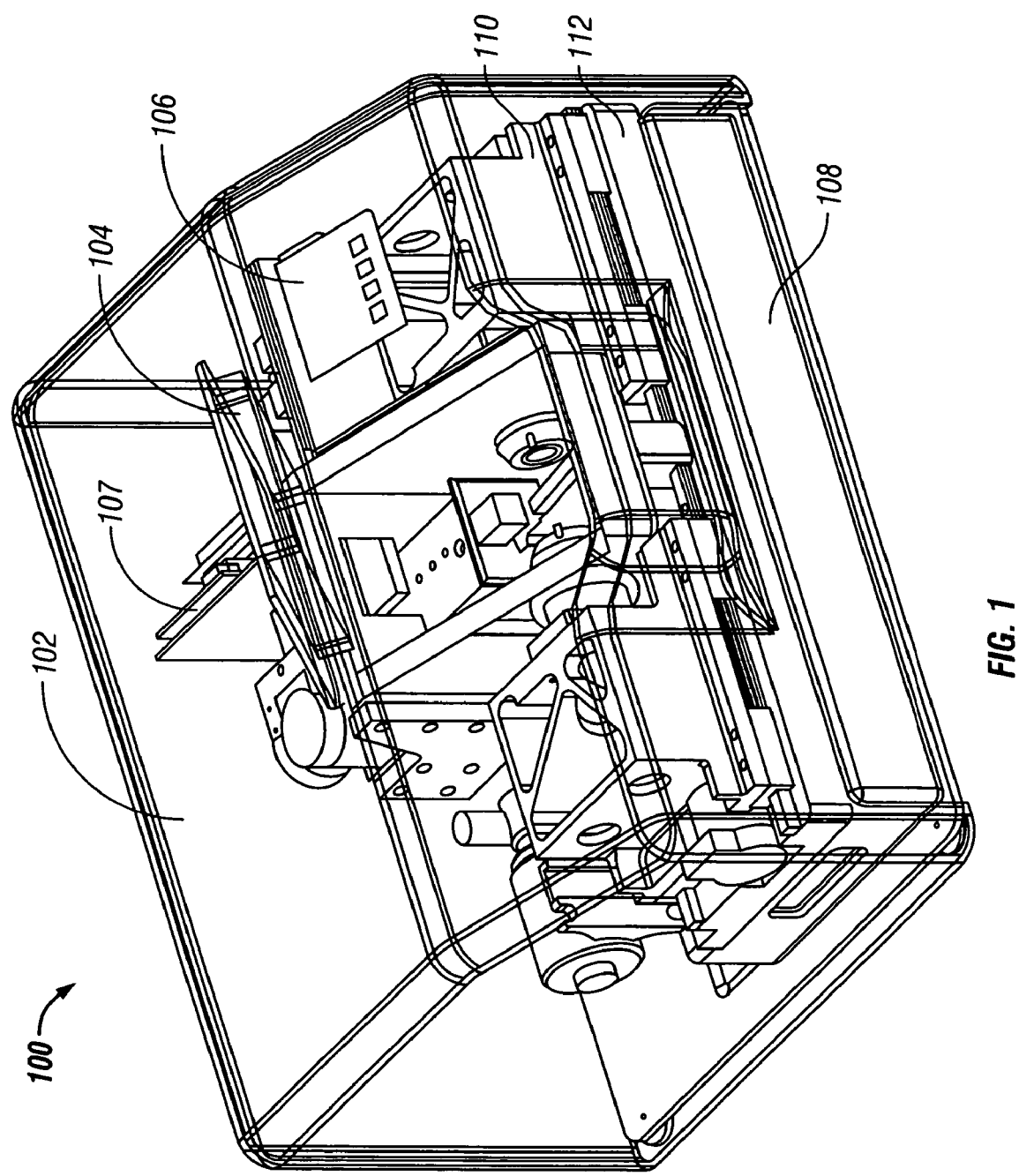
FIG. 1 is a perspective view of a milling machine that embodies the present invention.
Figure 2:
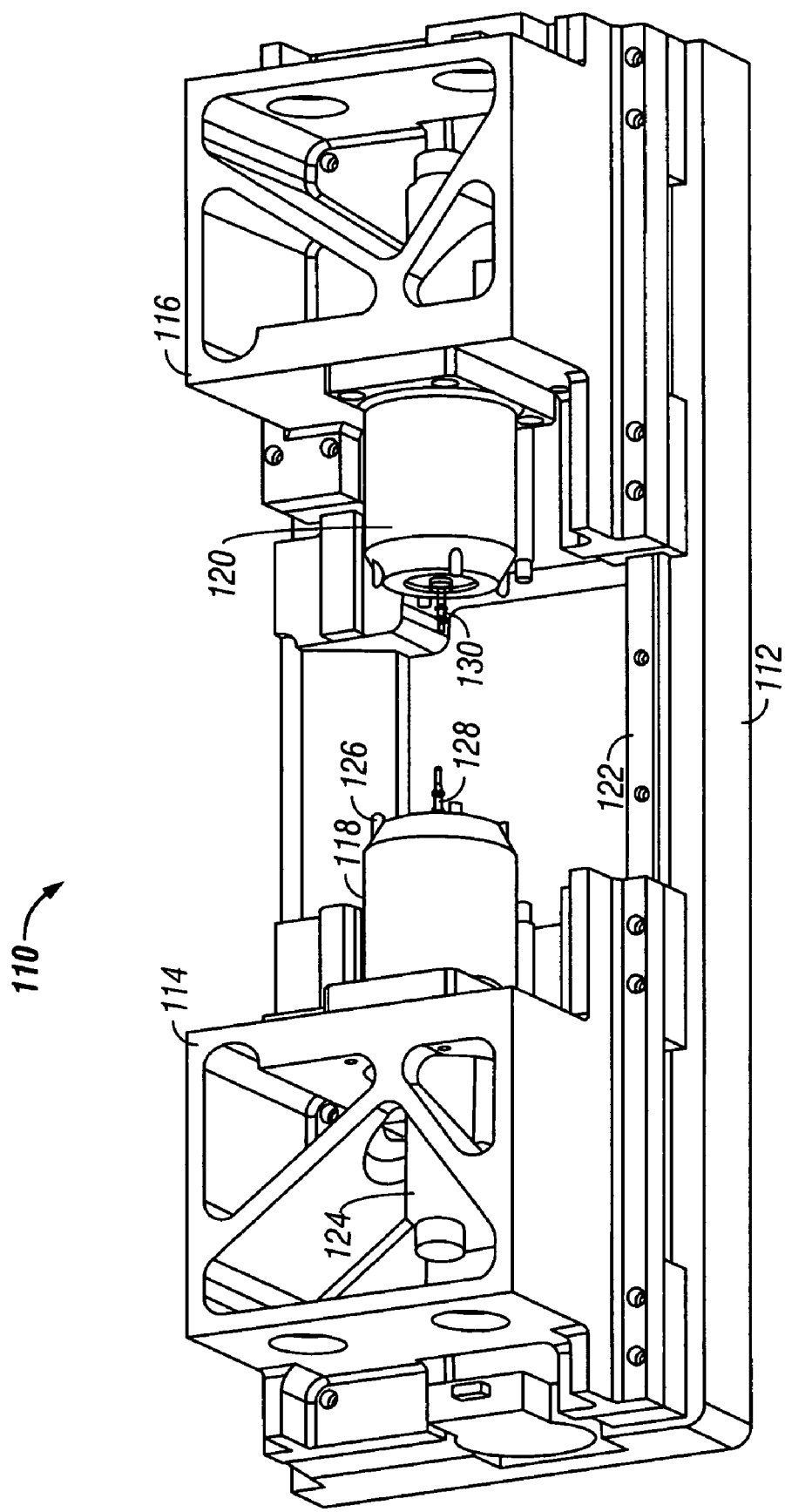
FIG. 2 is perspective showing the carriage that controls the x-axis movement of the spindles.

FIGS. 1 and 2 provide perspective views of the milling machine 100. It includes a cover 102 that protects the operator from the moving parts within. A blank 10 is held within a work area that is accessible through door 104. The x-axis carriage 110 is used to move the tools back and forth into engagement with the blank 10. The carriage 110 includes a first and second frame that both slide on rails on subframe 112. The subassembly 140 is used to control the y-axis and z-axis movement of the mandrel and blank. A reservoir is also located at the bottom of the machine 100. The CPU, memory and other electronics are located in compartment 107. These can be controlled, or activity displayed on display 106.

FIG. 2 is an isolated view of the x-axis carriage 110. It includes a first frame 114 and a second frame 116. In one embodiment, these frames are formed from a single block of metal, having no seams to decrease their stiffness. A first and second spindle 118, 120 are coupled to these frames 114, 116. The frames 114, 116 move on a single pair of rails 122 to ensure absolute alignment. Each frame is coupled to a first and second spindle, wherein each spindle has a central axis. The central axis of each spindle are aligned. Tools 128 and 130 are accepted into the spindles along this axis. The spindles rotate the tools so that a cutting surface on the tool can carve away material from the blank as desired. Of course, this process generates heat and carvings. A fluid stream emits from the spindle ports 126 as well to wash and cool the blank during milling. This effluent exits to a reservoir where particulate matter can settle. Motors 124 are used to supply the power to move the frames along the rails and to rotate the tools within the spindles.

Figure 3:
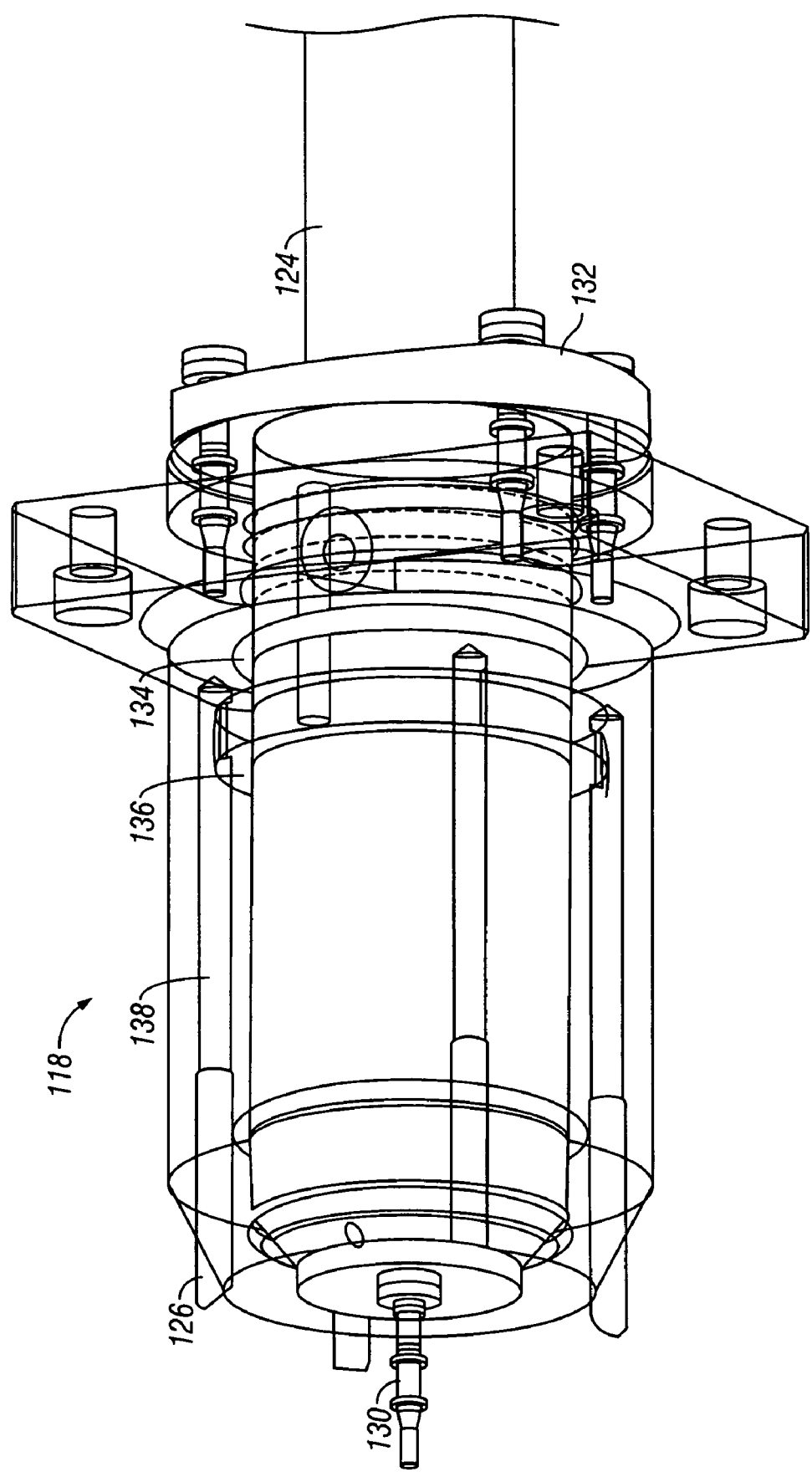
FIG. 3 is a cut-away view of the spindle showing the collet that engages the cutting tool and the cooling fluid delivery path.

FIG. 3 provides a more detailed view of the spindle 120 and the tool 130. Water, or other cooling fluid, is fed into the spindle through supply 124. Water passes through passages 132 into a collar 136. This collar supplies the water into several tubes 138 that carry the water to the front of the spindle. The water is sprayed from the tips of the tubes 138 and directed toward the tip of the tool 130. At least one o-ring is used to seal and separate the spindle's motor from the water.

Figure 4:
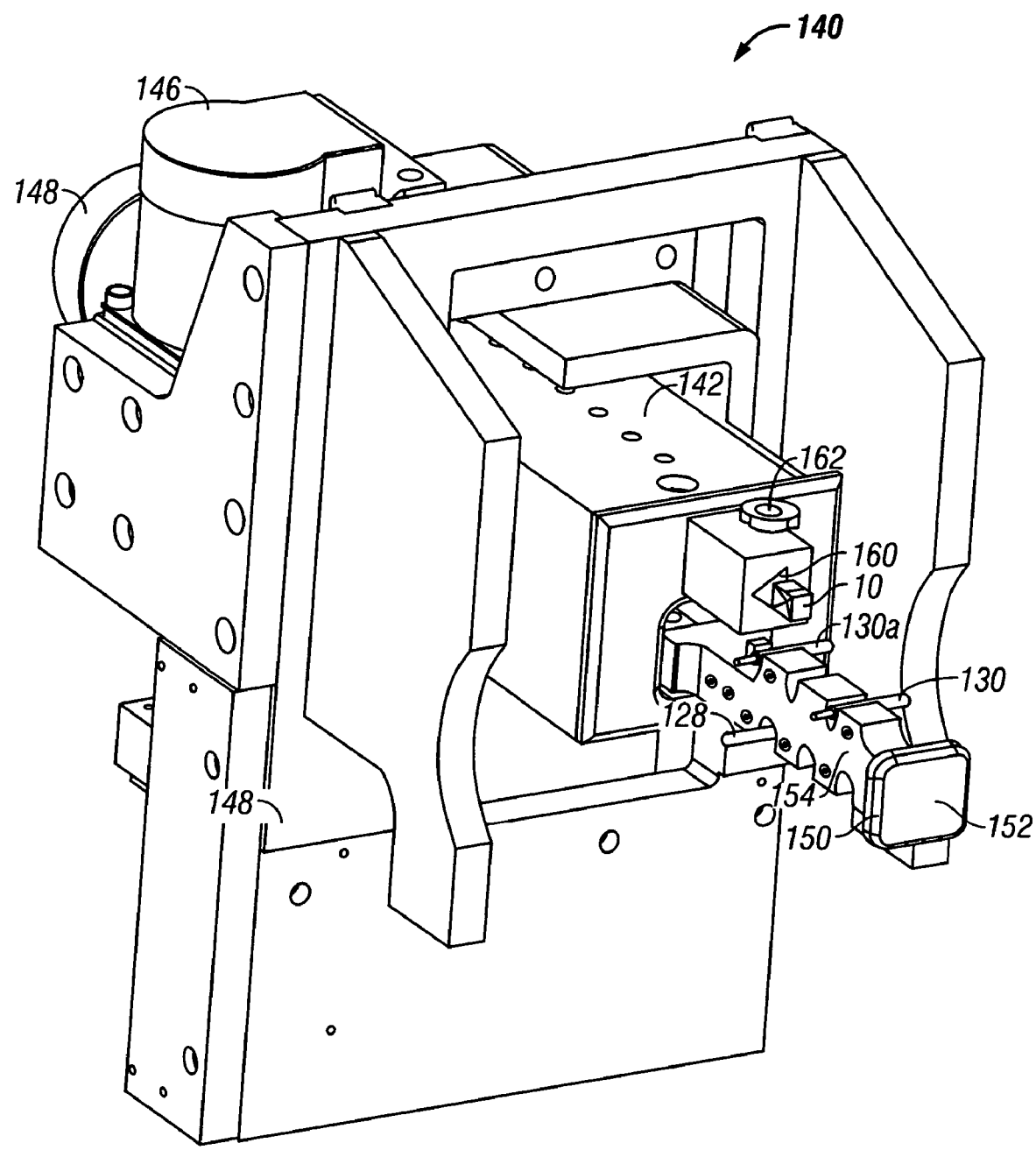
FIG. 4 is a perspective view of the subassembly that controls the y-axis and z-axis of the device.

The complex outer contour of the damaged tooth is reproduced by the present milling machine. This requires an accurate understanding of exactly the location of the tip of the tools and the x, y, z coordinates of the blank. Thus the shape and length of the mandrel 160 holding the blank must be precise. Very precise motors are used to move the carriages shown in FIG. 3. This same level of precision is reproduced for the y and z axes. However, rather than move the spindles, the mandrel is moved in the y and z axes by the subassembly 140 shown in FIG. 4. In FIG. 4, the y-axis is controlled by moving a carriage along rails. A separate z-axis carriage 142 includes the frame for engaging the mandrel 160 and automatic tool changer 130. This view also illustrates the location of the mandrel 160 and blank 10 to be milled. It is located on the z-axis carriage. A cam 162 is used to secure the mandrel in place. The mandrel and blank will be shown in greater detail below. The automatic tool changer 150 is also attached to the z-axis carriage. The tool changer can carry several additional tools 128, 130 for placement into the spindles. The tool changer 150 also includes at least one open port 154 for accepting the tool in the spindle. An electronics package 152 can be located on the end of the tool changer 150.

Figure 5:
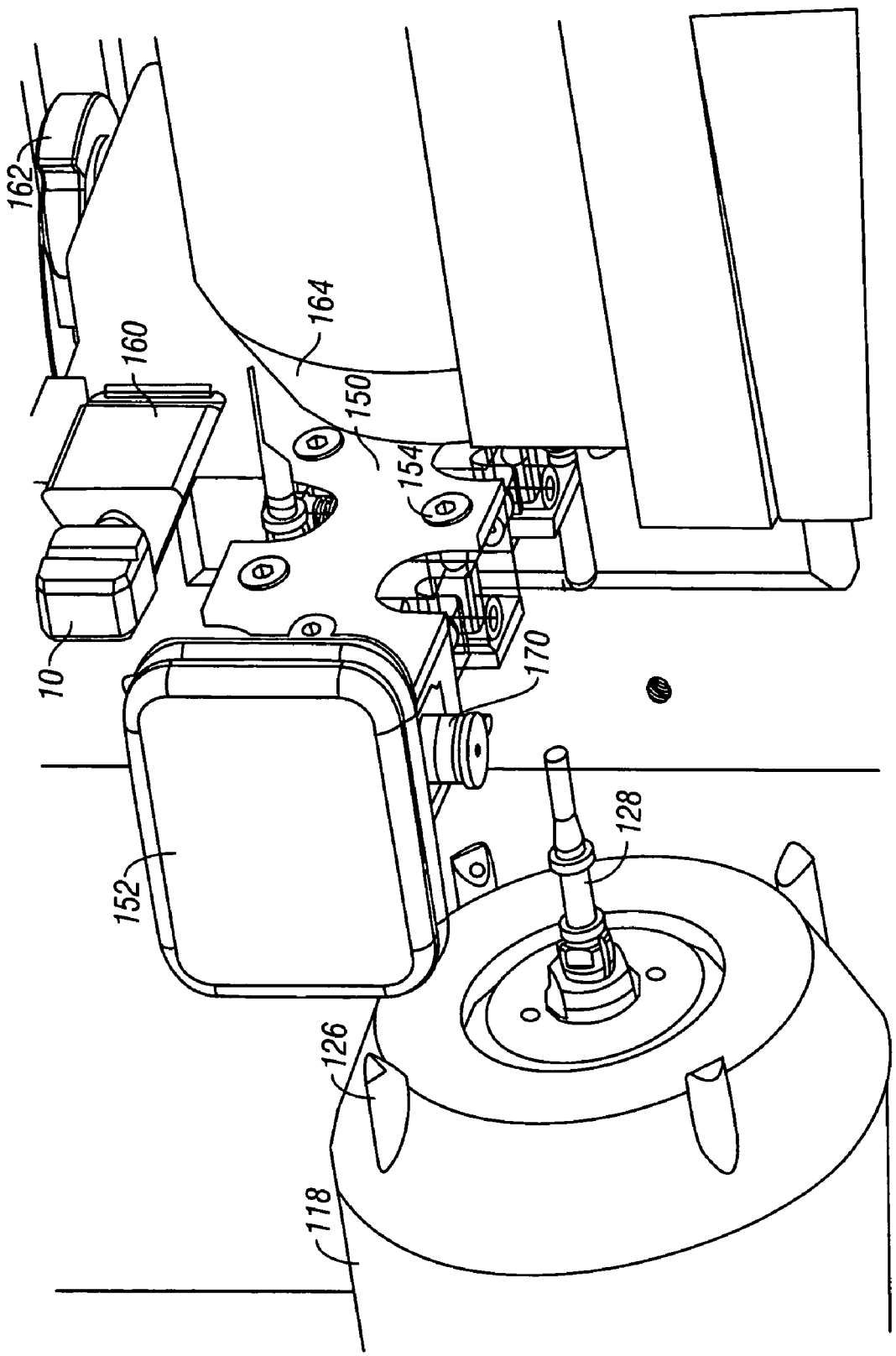
FIG. 5 is an enlarged view showing the automatic tool changing machine and the digital camera used to detect tool wear and axial calibration.

FIG. 5 provides an even more detailed view of the tool changer 150, blank 10, and tools. In this view, the y-axis carriage has moved the blank 10 above the tool 128. In this position, a camera 170 can be used to inspect the condition of the tip of tool 128. Note that the tool 128 is co-axially located within the spindle 118. Further, note that the nozzles 126 are angled to direct a cooling spray of fluid onto the tip of the tool 128.

Figure 6:
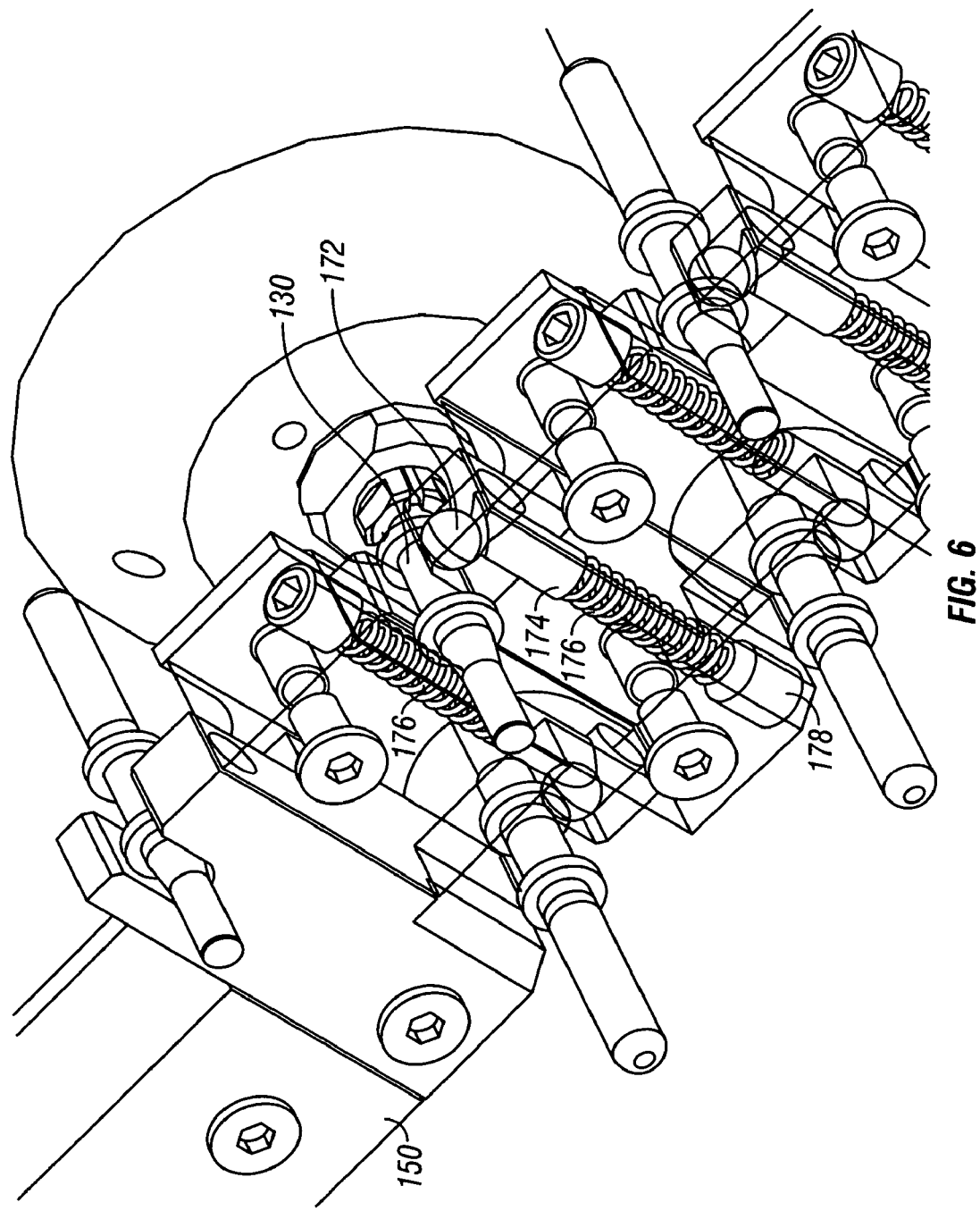
FIG. 6 is an enlarged perspective showing the engagement between the tool in a spindle and the automatic tool changer.

One of the important advances of the present invention is the ability to substitute tools as required. For example, a tool for grinding a contour onto a ceramic is different than a tool for grinding a contour onto a blank of gold. The prior art has never addressed the need for a lab to be able to quickly deal with blanks of differing materials. The present invention can allow a technician to simply enter the desired material. The milling machine will engage the appropriate tool for the material. The camera 170 will inspect the tool for wear and if necessary, select a backup tool for the process. Alternatively, if the tool is too worn and no back-up is available, the technician will be alerted. The ability to engage and disengage the tools is shown in FIG. 6. The tool changer 150 is positioned with the y-axis carriage to a position in between the spindles. The selected tool is positioned in co-axial relationship with the spindle using the z-axis carriage. A collet on the spindle is opened to engage the distal end of the tool, for example tool 130. The tool is releasably secured in the tool changer 150 with a spring loaded ball 172 or other means for securing the tool. Ball 172 presses against a central portion of the tool between a first and second flange. When the tool is engaged in the spindle, its collet closes. The tool changer 150 is then lowered with the y-axis carriage. This forces the ball 172 against pin 174 and compressed spring 176. The force on spring 176 can be adjusted using the set screw 178.

Figure 7:
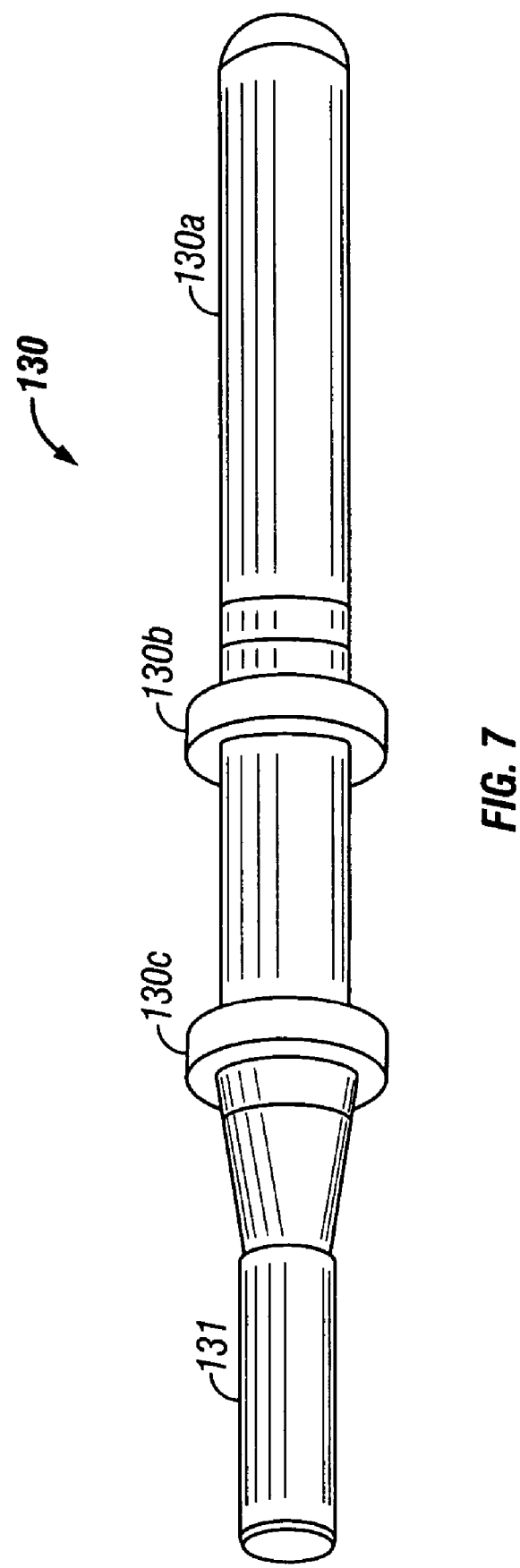
FIG. 7 is a perspective view of a tool that can be used in the present embodiment.

FIG. 7 provides a more detailed illustration of the tool 130. It includes a distal end 130a that is engaged within the spindle. At least 25% of the length of the tool is engaged within the spindle to ensure stability and to minimize and bending of the tool. The proximal end 131 of the tool can vary based on the material to be milled. For example, the grinding tip shown is for a ceramic. However, another tip might be used for grinding away a metal blank. Flanges 130b and 130c define a central portion that is used to engage the tool to the tool changer 150. However, the flanges serve the additional purpose of assisting with the registration of the tool and the blank. In other words, even though the exact length of the tool is known, the x, y, z coordinates of its tip must still be known exactly. When the tool is engaged into the spindle, the flange acts as a travel limit and thus defines the distance between the tip and the spindle. Thus, when the spindle moves along the x-axis, the position of the tip of the tool will be known.

Figure 8:
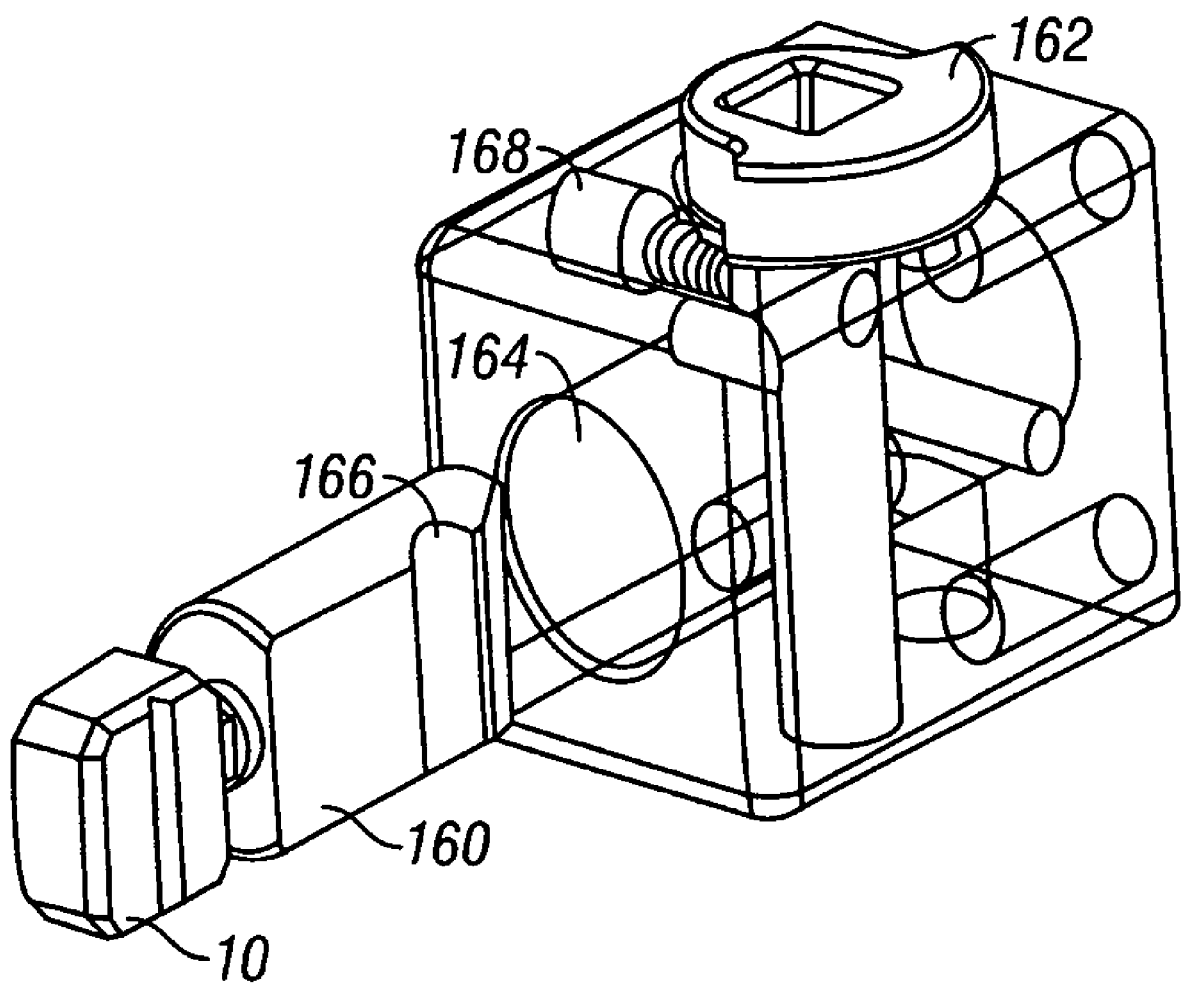
FIG. 8 is an exploded view of the mandrel and blank.

In addition to knowing the exact x, y, and z coordinates of the tool tips, it is also essential to know the exact position of the blank. This requires that the mandrel and blank are consistently placed into the machine. The mandrel and blank engage a mandrel socket 164 that in turn engages the z-axis carriage. FIG. 8 shows the mandrel socket in more detail. The mandrel 160 has a distal end that enters a similarly shaped socket 164. As shown the mandrel has a generally circular cross-section that engages the generally cylindrical socket. A groove 166 near the distal end of the socket provides an engagement surface for a cam 162. The cam 162 is rotated to a first position to allow insertion of the mandrel 160. The cam 162 is then rotated to a second position that engages the groove and secures the mandrel within the socket. A pin 168 is used to prevent the accidental rotation of the cam. While a cylindrical mandrel is shown, its cross-section could be any suitable shape. Note that the socket has an opening on both ends. This allows for debris to be pushed through the socket rather than allow it to build up within the socket.

While various embodiments of the invention have been described, it will be apparent to those of ordinary skill in the art that many more embodiments and implementations are possible within the scope of the invention. Accordingly, the invention is not to be restricted except in light of the attached claims and their equivalents

We claim:

1. A milling machine for milling a blank comprising
   (a) an x-axis carriage having a first and second spindle, which are each operable to translate independently along an x-axis,
      i) said first spindle having a first central axis and operable to receive a first tool in line with said first central axis and
      ii) said second spindle having a second central axis and operable to receive a second tool in line with said second central axis and in an opposing orientation to said first tool;
      wherein said first and second central axes are axially aligned and parallel to said x-axis;
   (b) a subassembly mechanism operable for holding and adjusting the position of said blank, comprising;
      i) a y-axis carriage operable to translate independently along a y-axis and;
      ii) a z-axis carriage contained within said y-axis carriage and operable to translate independently along a z-axis.

2. The milling machine of claim 1 wherein the x-axis carriage further comprises a pair of rails for aligning and translating said first and second spindles along said x-axis.

3. The milling machine of claim 1 wherein the spindles each comprise a motor for rotating said tool when received and coupled to its respective spindle.

4. The milling machine of claim 1 wherein at least one spindle comprises a means for delivering a cooling fluid to the blank.

5. The milling machine of claim 4 wherein the means for delivering comprises at least one fluid jet.

6. The milling machine of claim 5 wherein the fluid jet obtains a cooling fluid from a reservoir located beneath the milling machine.

7. The milling machine of claim 6 wherein the reservoir allows for the settlement of particulate located within the fluid.

8. The milling machine of claim 1 further comprising said first and second tools received and coupled into the first and second spindles, respectively.

9. The milling machine of claim 1 further comprises a tool changer for storing at least one replacement tool.

10. The milling machine of claim 1 further comprises a camera.

11. The milling machine of claim 10 wherein the camera is positioned to view said first and second tools.

12. The milling machine of claim 10 wherein the camera is a CCD camera.

* * * * *